United States Patent [19]

Gilligan et al.

[11] Patent Number: 4,708,934

[45] Date of Patent: Nov. 24, 1987

[54] α-AMIDATION ENZYME

[75] Inventors: James P. Gilligan, Elizabeth; Barry N. Jones, Bloomingdale, both of N.J.

[73] Assignee: Unigene Laboratories, Inc., Fairfield, N.J.

[21] Appl. No.: 655,366

[22] Filed: Sep. 27, 1984

[51] Int. Cl.$^4$ .................. C12P 21/00; C12P 21/06; C12P 21/02; C12N 9/80; C12N 15/00

[52] U.S. Cl. ........................... 435/68; 435/69; 435/70; 435/228; 435/172.3; 935/11; 935/51

[58] Field of Search ............... 435/68, 227, 228, 240, 435/253, 172.3, 69, 70; 935/14, 51, 70, 71, 73

[56] References Cited

PUBLICATIONS

Eipper et al, *Proc. Natl. Acad Sci*, vol. 80, pp. 5144–5148, 1983.
Eipper et al, *Peptides*, vol. 4, pp. 921–928, 1983.
Bradbury et al., *Nature*, vol. 298, pp. 686–688, 1982.
Hsueh et al, in *Proteases, Potential Role in Health and Disease*, Plenum Press, New York and London, (Hörl & Heidland, eds.) pp. 141–151, 1984.
Amara et al, *Proc. Natl. Acad Sci*, vol. 77, pp. 4444–4448, 1980.
Pharmacia Fine Chemicals Catalogue, 1984, p. 9.
Glembotski et al, *J. Biol. Chem*, vol. 259(10), pp. 6385–6392, 1984.
Chem Abst., p. 244, 101:50587w.
Mains et al, *Endocrinology*, vol. 116, pp. 2505–2515, 1985.
Eipper et al, *Endocrinology*, vol. 116, pp. 2497–2504, 1985.

*Primary Examiner*—Thomas G. Wiseman
*Assistant Examiner*—Jayme A. Huleatt
*Attorney, Agent, or Firm*—Ostrolenk, Faber, Gerb & Soffen

[57] ABSTRACT

Peptidyl-glycine α-amidating monooxygenase is an enzyme extractable from medullary thyroid carcinoma cell lines and tissue samples, having a molecular mass of about 60,000 to 65,000 daltons. It has been purified so as to exhibit a single, homogeneous, well-defined band using electrophoretic procedures performed on SDS-polyacrylamide gels, and has a specific enzymatic activity of at least 50 mU per mg protein. The free or immobilized enzyme, in the presence of $Cu^{+2}$ ions, ascorbate, and oxygen, can be used to prepare an α-amidated protein from a polypeptide substrate possessing a carboxyl-terminal glycine residue. The purified enzyme can be used as an antigen in order to produce enzyme-specific monoclonal antibodies, and can provide the information necessary to design and construct prokaryotes or other appropriate unicellular organisms or host cells isolated from multicellular organisms which possess peptidyl-glycine α-amidating capability.

7 Claims, No Drawings

α-AMIDATION ENZYME

BACKGROUND OF THE INVENTION

The intracellular processing (cleavage and/or functional group modification) of precursor forms of native proteins following their translation from nucleic acid coding sequences has been clearly documented.

In general, mammalian cells and other eukaryotes can perform certain post-translational processing procedures, while prokaryotes can not. Certain prokaryotes, such as E. coli, are widely employed as hosts for the production of mammalian proteins via recombinant DNA (rDNA) technology because they can be readily grown in batch fermentation procedures and because they are genetically well-characterized. However, many mammalian proteins produced by genetic engineering technoloy require some type of post-translational processing, and this must often be accomplished by using complex, in vitro chemical or enzymatic procedures which are cost-prohibitive for large-scale production applications.

One type of processing activity involves the specific amidation (conversion of —COOH group to a —CONH$_2$ group) of the carboxyl-terminal amino acid of a protein. Many naturally-occurring hormones and peptides contain such a modification, which is often essential if the protein is to be biologically active. An example is calcitonin, where the substitution of a non-amidated proline residue for the amidated proline of the native form results in a 3,000-fold reduction in biological activity.

The agent which effects this C-terminal (alpha) amidation recognizes a glycine residue which immediately follows the amino acid to be amidated (R-X-gly, where R is the main body of the protein, X is the residue which is amidated, and "gly" is the glycine residue). The glycine is cleaved and actually donates the amino moiety to the penultimate amino acid, thereby amidating it.

Enzymatic preparations capable of amidating the carboxyl-terminus of peptides and proteins have been described from a variety of sources. For instance. Bradbury, A. F., et al, Nature 298, 1982, p. 686–688 report an α-amidating enzyme activity to be present in porcine pituitary.

Husain, I., and Tate, S. S., FEBS Letters, Vol. 152, #2, 1983, p. 277–281, described an α-amidating activity present in bovine pituitary neurosecretory granules.

Eipper et al, PNAS Vol. 80, 1983, p. 5144–5148, reported an α-amidating enzyme activity to be present in the anterior, intermediate and posterior lobes of the rat pituitary gland.

Gomez et al, FEBS Letters, Vol. 167, #1, 1984, p. 160–164 determined that rat hypothalamus also contained an α-amidating enzyme activity.

Bradbury, A. F., Smythe, D. G., in Peptides Structure and Function: Proceedings of the Eighth American Peptide Symposium; p. 249–52 (1983), Editors Hruby, V. J., and Rich, D. H., describe the presence of an α-amidating enzyme activity in rat thyroid glands.

Mains R. E. et al, Endocrinology, Vol. 114, 1984, p. 1522-1530, reported that a murine cell line derived from the anterior pituitary lobe (ATT-20) contained an α-amidating enzyme activity that apparently decreased with time in culture.

Glands or organs known to contain amidated peptides may contain an enzyme capable of catalyzing the amidation reaction. For example, lower life forms such as the dog fish (Squalus acanthias) have been reported by O'Donohue T. L., et al, Peptides 3, 1982, p. 353–395, to contain amidated peptides in pituitary extracts. Scheller, R. H. et al, Cell, Vol. 32, 1983, p. 7–22 reported the presence of amidation signal peptides in the marine snail Apylsia. Despite the apparent ubiquitous distribution of this activity in nature, little information has been published on its physicochemical characteristics. This may be attributed to the very low levels of enzyme present in these neuroendocrine organs.

Heretofore, the purification and characterization of the α-amidating enzyme have not been published. Physicochemical properties of partially purified enzyme preparations, however, have been reported.

The first authors to report an approximate molecular weight for the α-amidating enzyme were Bradbury A. F., et al, Nature, Vol. 298, 1982, p. 686–88. Using Sephadex G-100 they suggested a minimum apparent molecular mass of approximately 60,000 daltons.

Subsequent studies have suggested the molecular mass of the enzyme to be between 60,000 and 70,000 daltons. These include Husain, I., and Tate S. S., FEBS Letters, Vol. 152. #2, 1983, p. 277–281; Eipper B. A., PNAS Vol. (16), 1983 p. 5144–5148; Gomez et al., FEBS Letters , Vol., 167, #1, 1984, p. 160–64, and Kizer J. S., et al, PNAS, Vol. 81, 1984, p. 3228–3232.

Eipper et al, PNAS, Vol. 80, 1983, p. 5144–48, have reported that in addition to molecular oxygen, two cofactors are required for maximal enzyme activity; these are ascorbic acid and copper (II) ion.

The chemical reaction resulting in the amidation of the carboxyl-terminus of a peptide requires a source for the amino group. Bradbury, A. F., et al, Nature, Vol. 298, 1982, p. 686–688, demonstrated that glycine is cleaved and donates the amino moiety to the penultimate amino acid, resulting in the amidation of the latter. The requirement for glycine as the amino group donor has been substantiated by other authors.

Landymore, A. E. N., et al, BBRC Vol. 117, #1, 1983, p. 289–293 demonstrated that D-alanine could also serve as an amino donor in the amidation reaction. Subsequent work by Kizer et al, PNAS, Vol. 81, 1984, p. 3228–3232, showed two distinct enzyme activities in rat brain which were capable of catalyzing the α-amidating reaction. The higher molecular mass species (70,000 daltons) has a specificity restricted for glycine at the carboxyl-terminus of the substrate. The lower molecular mass enzyme accepts a substrate with β-alanine as the carboxyl-terminal amino acid.

The pH optimum for the α-amidating enzyme extracted and partially purified from porcine pituitary was reported by Bradbury A. F., and Smythe D. G., BBRC, Vol. 112, #2, 1983, p. 372–377 to be approximately 7.0. Eipper, B. A., et al, PNAS, Vol. 80, 1983, p. 5144–5148, corroborated these results by reporting a pH optimum of 7 for an α-amidating enzyme which was partially purified from rat pituitaries. They also noted that enzyme activity declined rapidly at pH levels below 6.5 or above 7.5.

In all of the aforementiond publications, which are incorporated herein by reference the extracts and partially purified enzyme mixtures contained additional proteolytic enzymes which degrade the potential substrate and products as well as the α-amidating enzyme.

It is therefore the object of the invention to provide a purified α-amidating enzyme which can efficiently be used to produce α-amidated peptides from peptide or polypeptide substrates, to prepare monoclonal antibodies specific for the enzyme, and to construct prokaryotes or other appropriate unicellular organisms or host cells isolated from multicellular organisms containing heterologous DNA coding for the enzyme. This and other objects of the invention will become apparent to those skilled in this art from the following detailed disclosure.

SUMMARY OF THE INVENTION

This invention relates to a purified α-amidating enzyme, its uses, monoclonal antibodies specific for the enzyme, and prokaryotes or other unicellular organisms or host cells isolated from multicellular organisms containing heterologous genetic material which codes for the enzyme. More particularly, the invention is concerned with purified peptidyl-glycine α-amidating monooxygenase, which is an enzyme extractable from medullary thyroid carcinomas, which has molecular mass of about 60,000 to 65,000 daltons, which has been purified so as to exhibit a single, homogeneous, well-defined band by electrophoretic procedures performed on SDS/polyacrylamide gels, and which has a specific enzymatic activity of at least 50 mU per mg protein. [1U=the conversion of 1 micromole of Dansyl-D-Tyr-Val-Gly-COOH to 1 micromole of Dansyl-D-Tyr-Val-CONH$_2$ per minute at 37° C. and pH 7.0.] The invention also provides a method of preparing an α-amidating peptide from peptide or polypeptide substrates containing a terminal glycine residue by reacting the substrate with oxygen in the presence of the free or immobilized purified enzyme, ascorbate and copper. The invention further provides for the production of monoclonal antibodies to the purified enzyme and for the development of prokaryotes, other unicellular organisms or host cells isolated from multicellular organisms containing a heterologous DNA coding for peptidyl-glycine α-amidating monooxygenase.

DESCRIPTION OF THE INVENTION

It has now been discovered that homogeneously-purified α-amidating enzyme can be obtained through a multi-step procedure employing a combination of size exclusion and ion exchange chromatography from solid tumor tissue extracts, tumor cell-lines, and the tissue culture medium from such cell lines.

The enzyme has been extracted from rat medullary thyroid carcinomas developed in WAG/Rij Wistar rats as described by Roos, B. A., et al, Endocrinology, 1979, Vol. 150, #1, p. 27–32. This tissue has been deposited as IVI-10028. The enzyme has also been extracted from other sources, notably human and rat medullary thyroid carcinoma cell lines. The rat cell line 77(74) was derived from rat medullary thyroid carcinoma tumors by serial passages as described by Muszynski, M. et al, JBC 1983, Vol. 258, pp. 11678–83. This cell line has been deposited as IVI-10029. A human cell line HTT 54(34) was developed by B. A. Roos at the VA Medical Center in Cleveland, Ohio using human medullary thyroid carcinoma cells for the primary culture. The human cell line HTT 54(34) has been deposited as IVI-10031. Defined tissue culture media from both the human and rat cell lines have been demonstrated to contain significant levels of α-amidating enzyme activity, indicating that a portion of the enzyme is secreted from the cells.

The enzyme is obtained and purified by first subjecting the crude material to anion exchange chromatography. The sample, for example, can be bulk-loaded on a preparative scale anion exchange column such as a DE-52 resin from Whatman, Limited. The α-amidating activity-containing product is then subjected to size exclusion chromatography on a resin of appropriate resolving capabilities, for example a Sephacryl S-200 superfine column which is available from Pharmacia Fine Chemicals. The activity-containing eluant fraction is then subjected to ion exchange chromatography using a strong anion exchange matrix. A resin which may be used is the Mono Q HR5/5 strong anion exchange resin from Pharmacia Fine Chemicals and one or more passes on the column may be required for homogeneous purification of the enzyme. Each purification step can be monitored for both protein content and the level of α-amidation activity. This information is used to calculate the specific activity of the enzyme which serves as an indicator of the relative purity of the enzyme.

The resulting enzyme is peptidyl-glycine α-amidating monooxygenase (deposited rat derived enzyme, IVI-10032; deposited human derived enzyme, IVI-10033) which has a molecular mass of about 60,000 to 65,000 daltons. It has been purified such that it exhibits a specific enzymatic activity (number of units of α-amidation activity per milligram of protein) of at least approximately 25 mU and preferably at least approximately 50 mU/mg protein. It has also been purified so as to exhibit a single, homogeneous, well-defined band following electrophoresis on sodium dodecyl sulfate/polyacrylamide gels (SDS-PAGE).

The purified peptidyl-glycine α-amidating monooxygenase is used to amidate the alpha-carboxyl group of a polypeptide having a terminal glycine residue, where the glycine functions as an amino group donor. The substrate peptide or polypeptide can be purified from natural sources, synthesized from its component amino acids, or produced by recombinant DNA techniques. The glycine-terminating polypeptide is combined with oxygen in the presence of an effective amount of the enzyme. The amount of the enzyme required depends on several variables well known to this art including particularly, but not limited to, the following: the specific activity of a given enzyme preparation, the amount and chemical nature of the substrate to be converted, the time within which conversion is to take place and the temperature and pH of the reaction mixture. Those skilled in this art will recognize other variables that may influence the precise amount of enzyme required in a given situation. The oxygen is usually employed in stoichiometric amount but an excess of the oxygen does not affect the reaction. The presence of copper ions is also required, and can be provided by any copper salt whose anion does not adversely affect the reaction. When the enzyme has a specific enzymatic activity of about 1 mU/mg protein, maximum α-amidation occurs with a concentration of 4.7 uM cupric ions. As the purity of the enzyme is increased, the concentration requirements for the exogenous cupric ion diminishes. The enzymatic activity can also be enhanced by the presence of ascorbate ions which can be provided by any salt, as long as the cation of the salt does not adversely effect the reaction. For purified enzyme having a specific enzymatic activity of approximately 50 mU/mg protein, maximal acitivity of the α-amidation occurs at about 5.5 mM ascorbate. α-amidation activity may be increased by the addition of catalase. The α-amidation reaction optimum pH is between 6.5 and 7.5.

Since the peptidyl-glycine α-amidating monooxygenase has been sufficiently purifed, it is now possible to obtain monoclonal antibodies directed against the enzyme by standard procedures. The monoclonal antibodies allow the enzyme recovery procedures from the medullary thyroid carcinomas to be facilitated or wholly supplanted by immunoabsorption purification procedures. The enzyme has also been sufficiently purified to permit its amino acid sequence to be determined. This information is necessary in order to permit the isolation of the genetic material coding for the enzyme and its subsequent incorporation into an appropriate unicellular organism or host cell isolated from a multicellular organism which does not contain DNA coding for the peptidyl-glycine α-amidating enzyme. This is accomplished by standard recombinant DNA procedures, such as found in Maniatis, E. F., et al, Molecular Cloning: A Laboratory Manual, Cold Spring Harbor, 1982; or Wu, R., ed., Methods in Enzymology, Vol. 68, Academic Press, 1979. The resulting cells containing the heterologous DNA coding for peptidyl-glycine α-amidating enzyme allows the production of sufficient quantities of the enzyme in order to perform in vitro post-translational α-amidation and theoretically permits these cells to perform this modification of a peptide or polypeptide in vivo.

The α-amidation activity of the purified enzyme of this invention was demonstrated using a substrate of radioiodinated D-Tyr-Val-Gly, a peptide whose sequence mimics the carboxyl terminus of the melanocyte stimulating hormone precursor. Assays were performed in 100 mM TES (N-tris[hydroxymethyl]methyl-2-aminoethane sulfonic acid) buffer, pH 7.0, at 37° C. for three hours. Th product, [$^{125}$I]Tyr-Val-NH$_2$, was separated from the substrate by cation exchange chromatography. The amidating enzyme activity was also demonstrated using a synthetic substrate which mimicked the sequence of the carboxyl terminus of calcitonin, [Tyr$^{25}$-Gly$^{33}$] calcitonin (26–32).

Although the present invention has been described in connection with preferred embodiments thereof, many variations and modifications will become apparent to those skilled in the art.

What is claimed is:

1. A method of preparing an alpha-amidated peptide or polypeptide from a peptide or polypeptide substrate having a terminal glycine residue having an alpha-carboxyl group comprising reacting said substrate in the presence of an enzymatically effective amount of a purified enzyme preparation containing peptidyl-glycine alpha-amidating monooxygenase, PAM, said substrate purified from natural sources or produced by recombinant DNA techniques and said enzyme preparation capable of amidating the alpha-carboxyl group of the substrate, said preparation having a specific enzymatic activity of at least 25 mU/mg protein (as measured by the conversion of Dansyl-D-Tyr-Val-Gly-COOH to Dansyl-D-Tyr-Val-CONH$_2$ at 37° C. and pH 7) and being substantially free of other proteolytic enzymes which degrade the peptide, the polypeptide, the amidated peptide or the amidated polypeptide, or PAM,
   wherein the purified enzyme preparation is prepared by a process comprising:
   (a) subjecting a PAM containing composition obtained from a medullary thyroid carcinoma tissues, cell lines thereof, or tissue culture media from such cell lines to anion exchange chromatography and then size exclusion chromatography to produce a PAM containing eluant fraction; and
   (b) subjecting the eluant fraction to strong anion exchange chromatography to produce the purified enzyme preparation.

2. The method of claim 1, wherein the enzymatic activity is at least 50/mU/mg protein.

3. The method of claim 2, wherein the purified enzyme preparation is homogeneous.

4. The method of claim 1, 2, or 3, wherein the medullary thyroid carcinoma is derived from a rat.

5. The method of claim 4, wherein the rat medullary thyroid carcinoma is deposit IVI-10028, and the cell line is deposit IVI-10029.

6. The method of claim 1, 2, or 3, wherein the PAM has a molecular mass of 60,000 to 65,000 daltons.

7. The method of claim 2 or 3, wherein the purified preparation exhibits a single, homogeneous, well defined band following electrophoresis on SDS/polyacrylamide gel.

* * * * *